United States Patent [19]

Eberbach

[11] Patent Number: 5,141,515
[45] Date of Patent: * Aug. 25, 1992

[54] APPARATUS AND METHODS FOR REPAIRING HERNIAS

[76] Inventor: Mark A. Eberbach, 4234 Winding Willow Dr., Tampa, Fla. 33624

[*] Notice: The portion of the term of this patent subsequent to Jun. 16, 2009 has been disclaimed.

[21] Appl. No.: 595,956

[22] Filed: Oct. 11, 1990

[51] Int. Cl.$^5$ .............................................. A61B 19/00
[52] U.S. Cl. .................................. 606/151; 606/213; 128/887
[58] Field of Search ............... 606/110, 113, 114, 127, 606/151, 200, 213; 604/11, 12, 13, 14, 15; 623/12; 128/887

[56] References Cited

U.S. PATENT DOCUMENTS

| | | | |
|---|---|---|---|
| 460,940 | 10/1891 | Baugh | 606/106 |
| 736,744 | 8/1903 | Kratzmueller | 606/113 |
| 1,225,771 | 5/1917 | Clare | 606/113 |
| 1,275,520 | 8/1918 | Bell . | |
| 1,456,828 | 5/1923 | Pistor | 604/13 |
| 1,711,294 | 4/1929 | Weitzner | 128/887 |
| 3,152,466 | 10/1964 | Williams . | |
| 3,181,533 | 5/1965 | Heath | 606/113 |
| 3,706,311 | 12/1972 | Kokx . | |
| 3,857,395 | 12/1974 | Johnson et al. | 604/14 |
| 3,874,388 | 4/1975 | King et al. | 623/11 |
| 3,918,452 | 11/1975 | Cornfield | 604/11 |
| 4,007,743 | 2/1977 | Blake | 623/11 |
| 4,347,847 | 9/1982 | Usher | 606/151 |
| 4,519,643 | 5/1983 | Harris . | |
| 4,557,255 | 12/1985 | Goodman | 128/7 |
| 4,744,364 | 5/1988 | Kensey | 606/213 |
| 4,769,038 | 9/1988 | Bendavid et al. | 606/151 |
| 4,779,616 | 10/1988 | Johnson . | |
| 4,873,978 | 10/1989 | Ginsburg . | |
| 4,900,303 | 2/1990 | Lemelson | 606/213 |
| 4,909,789 | 3/1990 | Taguchi | 604/107 |
| 4,964,417 | 10/1990 | Peters | 128/887 |
| 5,021,059 | 6/1991 | Kensey et al. | 606/213 |

FOREIGN PATENT DOCUMENTS 53-94481 8/1978 Japan .

OTHER PUBLICATIONS

Francis Stock, "Repair of Large Hernia With Nylon Mesh" Feb. 20, 1954 The Lancet, vol. CCLXVI #6808 p. 395.

Primary Examiner—Stephen C. Pellegrino
Assistant Examiner—Glenn K. Dawson
Attorney, Agent, or Firm—Dominik, Stein, Saccocio, Reese, Colitz & Van Der Wall

[57] ABSTRACT

A method and system for the repair of hernias through laparoscopic techniques including plugging and patching, the system comprising a first assembly having a tubular sheath; a tubular plunger located within and moveable with respect to the sheath, the plunger having a distal end spaced proximally of the distal end of the sheath and a proximal end extending proximally of the proximal end of the sheath; a plug within the sheath at the distal end and moveable from interior thereof to exterior thereof upon manipulation of the proximal ends of the sheath and plunger by a surgeon. The system further comprising a second assembly having an other tubular sheath; an other tubular plunger located within and moveable with respect to the other sheath, the proximal end of the other plunger extending proximally outwardly of the other sheath for manipulation by a surgeon; elongated means extending through the other plunger and, at the distal end thereof forming a loop, the proximal end of the elongated means extending proximally outwardly of the other sheath for manipulation by a surgeon; and a patch supported on the loop for movement therewith.

17 Claims, 4 Drawing Sheets

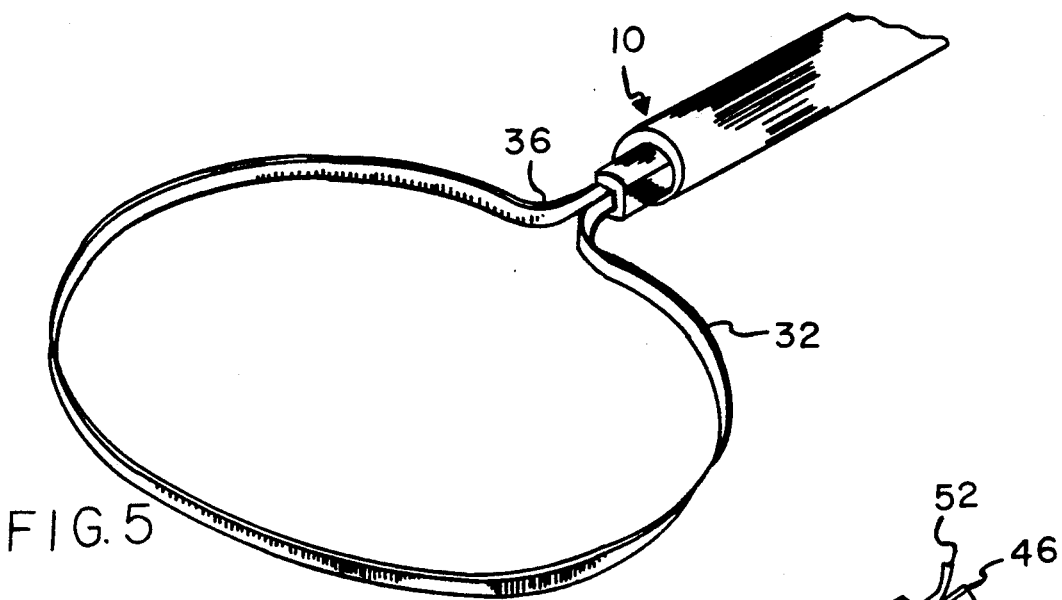
FIG. 5
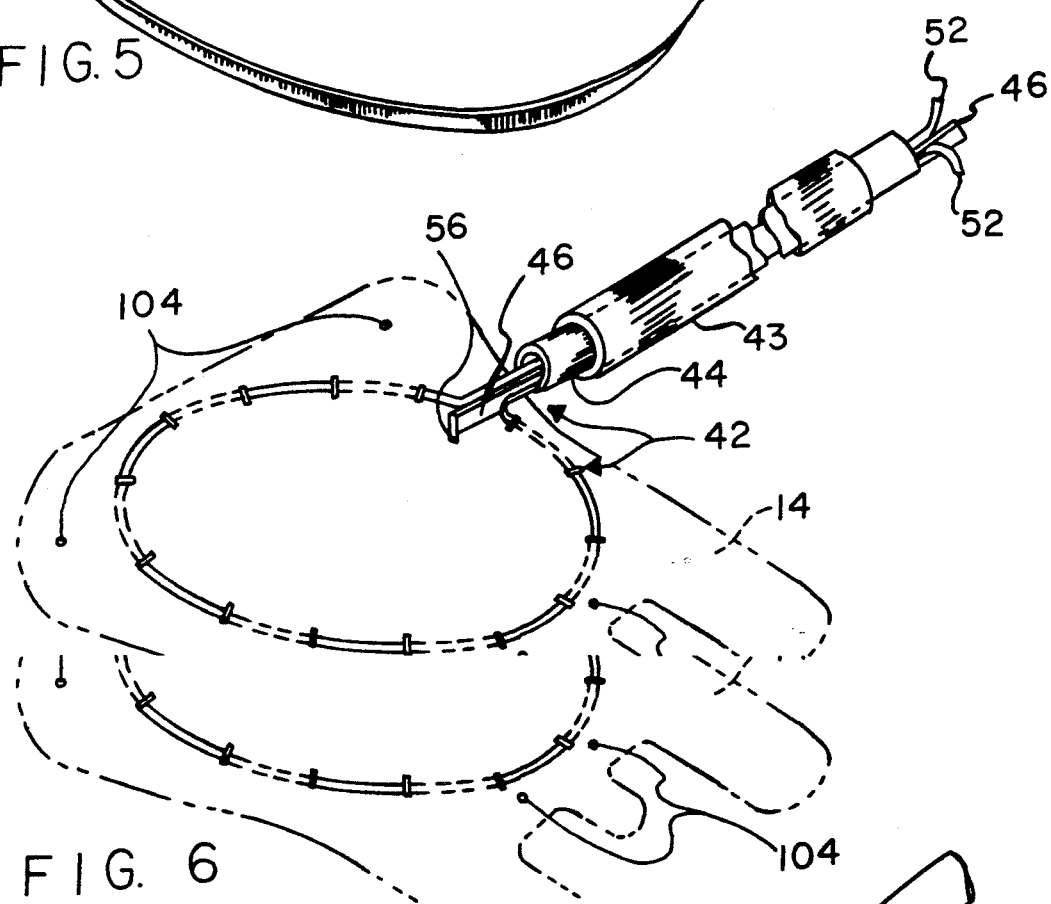
FIG. 6
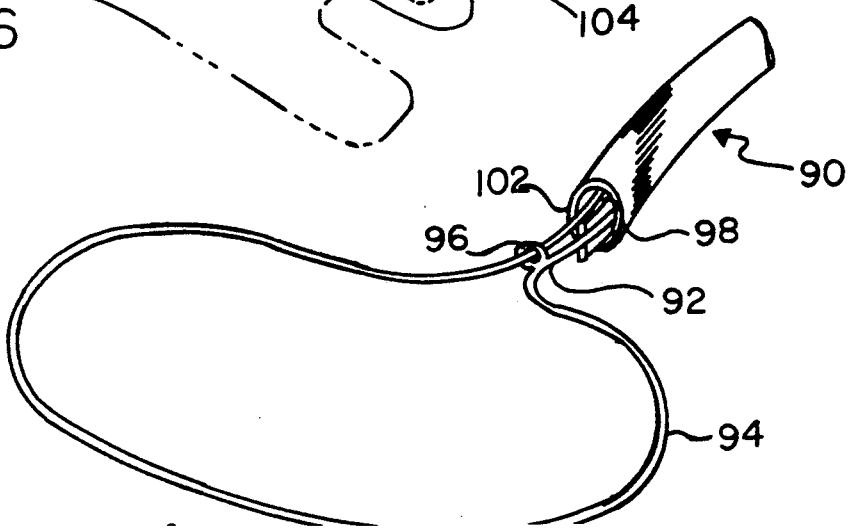

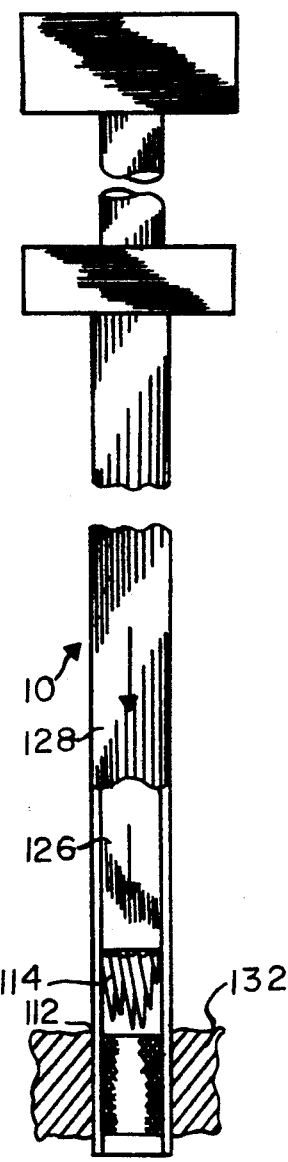
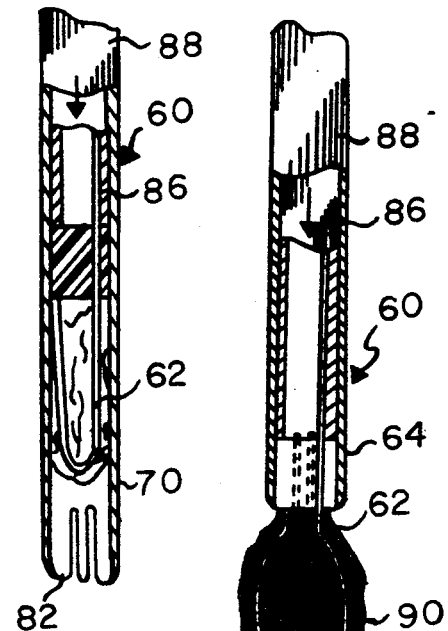
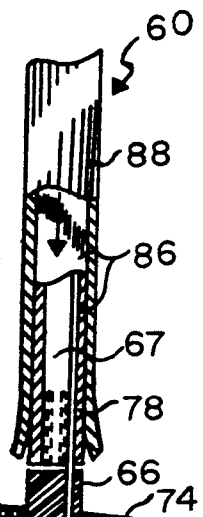
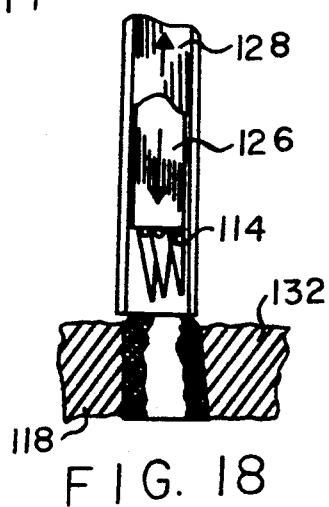
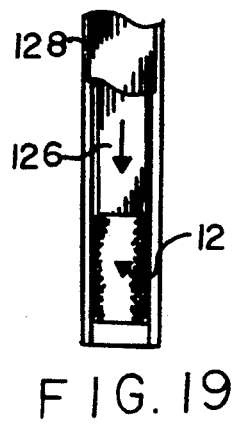

APPARATUS AND METHODS FOR REPAIRING HERNIAS

BACKGROUND OF THE INVENTION

1. Summary of the Invention

This invention relates to medical apparatus and methods and, more particularly, to the repair of hernias with a laparoscopic approach and associated plugs and patches.

2. Summary of the Background Art

A hernia is one of the most common ailments of mankind. Approximately five percent of the adult male population is affected. Basically, a hernia is a weakness or hole in the abdominal wall through which abdominal contents such as bowels may protrude. Inguinal or groin hernias normally occur at one or more of three locations. The first location in the weakened wall or inguinal floor of the abdomen in Hesselback's triangle. This type of hernia is called a direct hernia. An indirect hernia occurs at the internal ring adjacent to the vas deferens as it exits the abdomen to become part of the spermatic cord. The third is a femoral hernia that occurs adjacent and media to the femoral blood vessels.

All hernias represent a potentially life threatening condition and once diagnosed they should be repaired unless there is some contraindication.

The surgical repair of an inguinal hernia (inguinal herniorrhaphy) is a common procedure which surgeons often perform on an outpatient basis. It is estimated that 500,000 are performed each year in the United States. According to the procedure, an anesthetic is first administered to the patient and the surgeon then makes a large incision, about 6 inches, in the patient just above the inguinal ligament. Supporting abdominal muscle and fascia are dissected to reveal the hernia sac. The herniated contents protruding through the opening in the abdominal wall are returned to the abdomen. Thereafter, the surgeon closes the hernia sac. The local tissues are then sutured together from opposite sides of the weakened tissue, hole or hernia. The stretched or otherwise weakened tissue may be cut away. Where appropriate, a patch of artificial material may be sutured to the normal tissue to replace the stretched or otherwise weakened tissue or to reenforce over the outside of the repair. The incision is then closed over the repair. Recovery time necessary prior to heavy lifting or strenuous labour is usually six to eight weeks and recurrence rates may approach twenty percent.

Another more difficult approach which is less common, but more physiological, is to make an incision in the abdomen superior or cephalad to the hernia. The surgeon cuts through the abdominal wall to the last layer (the peritonium). Dissection continues in this preperitoneal approach and exposes the hernia defect from the inside. Again direct suture repair or patch repair may be performed. The recurrence rates are low with an inside patch repair because increased intra-abdominal pressure only serves to force the patch more firmly into place to plug the hole similar to a drain plug in a bathtub.

Although common, the standard operational procedures for repair of a hernia is undesirably lengthy and, consequently, costly, requires a large incision with the excessive dissection of normal tissue, causes excessive pain and discomfort to the patient, involves unacceptably long recovery and work disability time, and results in an unacceptably high recurrence rate.

Accordingly, it is an object of the present invention to provide a method and apparatus for the repair of hernias through laparoscopic techniques comprising a tubular sheath and a tubular plunger located within and moveable with respect to the sheath, the plunger having a distal end supporting a mending component adapted to be discharged from the sheath upon relative axial movement between the plunger and sheath, the plunger having an end extending proximally of the sheath for manipulation by a surgeon.

It is a further object of the present invention to employ laparoscopic techniques for the repair of hernias thereby reducing the length of the incision along with the unnecessary dissection of normal tissue.

It is a further object of the present invention to utilize a new laparoscopic approach via the preperitoneal space.

It is a further object of the present invention to minimize the time and cost of hernia operations.

It is a further object of the present invention to minimize the patient's pain and discomfort associated with a hernia operation.

It is a further object of the present invention to shorten the recovery time normally attendant with a hernia operation.

It is a further object of the present invention to reduce or preclude the recurrence of hernias.

Further objects of the present invention are to internally plug and or patch and restore stretched or weakened areas of an abdominal wall or overt hernia defects and to simultaneously patch all primary and secondary abdominal areas which are predisposed to hernias.

The foregoing has outlined some of the more pertinent objects of the present invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiments in addition to the scope of the invention defined by the claims taken in conjunction with the accompanying drawings.

SUMMARY OF THE INVENTION

The invention is defined by the appended claims with specific embodiments shown on the attached drawings. For the purpose of summarizing the invention, the invention may be incorporated into an improved apparatus for the repair of hernias through laparoscopic techniques comprising a tubular sheath and a tubular plunger located within and moveable with respect to the sheath, the plunger having a distal end supporting a mending component adapted to be discharged from the sheath upon relative axial movement between the plunger and sheath, the plunger having an end extending proximally of the sheath for manipulation by a surgeon. The mending component may be a plug or a patch.

The invention may also be incorporated into an apparatus for the plugging of hernias through laparoscopic techniques comprising a tubular sheath; a tubular plunger located within and moveable with respect to the sheath, the plunger having a distal end spaced proximally of the distal end of the sheath and a proximal end extending proximally of the proximal end of the sheath; and a plug within the sheath at the distal end and moveable from interior thereof to exterior thereof upon manipulation of the proximal ends of the plunger and sheath by a surgeon. The plug is generally cylindrical. The plug may include a flange on its proximal end. The flange includes two radially extending fingers with a recess therebetween.

The invention may also be incorporated into an apparatus for laparoscopically patching hernias comprising a tubular sheath; a tubular plunger located within and moveable with respect to the sheath, the proximal end of the plunger extending proximally outwardly of the sheath for manipulation by a surgeon; elongated means forming part of the plunger at the distal end thereof and forming a loop, the proximal end of the elongated means extending proximally outwardly of the sheath for manipulation by a surgeon; and a patch supported on the loop for movement therewith. The elongated means may be ribbon shaped and includes a worm gear for moving the elongated means with respect to the plunger and an enlargement at one end of the ribbon with a slot through which the elongated means passes to form the loop. The elongated means may be a thread including an eyelet formed in an intermediate portion of the thread through which the thread passes to form the loop. The loop may be formed of an absorbable material. The apparatus may further include means for securing the proximal end of the patch to the plunger. The apparatus further includes a guide rod as part of the plunger for guiding the movement of the ribbon with respect to the plunger during the blooming of the patch.

The invention may also be incorporated into a patch for positioning over the regions of a floor of an abdominal cavity normally susceptible to hernias, the patch having a proper anatomical and functional shape with a plurality of radially extending portions forming spaced recesses for the receipt of a vas deferens, testicular artery and vein and femoral vessels, the patch also having a passageway in a curved, symmetrical configuration for the receipt of a smoothly curved loop.

The invention may also be incorporated into a plug for positioning in hernia openings of an abdominal cavity and similar openings, the plug being of a cylindrical shape with a generally eliptical flange on the proximal end of the plug and two fingers extending radially from the flange with a recess therebetween.

The invention may also be incorporated into a system for the repair of hernias through laparoscopic techniques including plugging and patching, the system comprising a first assembly having a tubular sheath; a tubular plunger located within and moveable with respect to the sheath, the plunger having a distal end spaced proximally of the distal end of the sheath and a proximal end extending proximally of the proximal end of the sheath; a plug within the sheath at the distal end and moveable from interior thereof to exterior thereof upon manipulation of the proximal ends of the sheath and plunger by a surgeon; and the system further including a second assembly having another tubular sheath; another tubular plunger located within and moveable with respect to the other sheath, the proximal end of the other plunger extending proximally outwardly of the other sheath for manipulation by a surgeon; elongated means extending through the other plunger and, at the distal end thereof forming a loop, the proximal end of the elongated means extending proximally outwardly of the other sheath for manipulation by a surgeon; and a patch supported on the loop for movement therewith.

Lastly, the invention may also be incorporated into a method of repairing hernias through laparoscopic techniques comprising the steps of providing a tubular sheath and a tubular plunger located within and moveable with respect to the sheath; providing a mending component in the distal end of the sheath; effecting relative axial movement between the sheath and plunger to discharge and position the mending element.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific embodiments may be readily utilized as a basis for modifying or designing other methods and apparatus for carrying out the same purposes of the present invention. It should also be realized by those skilled in the art that such equivalent methods and apparatus do not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 5 is a perspective illustration of a portion of the introducer including an exterior sheath and plunger/expander assembly.

FIG. 6 is a perspective illustration of the patch of FIG. 4 with the patch introducer of FIG. 5 and with parts broken away to show certain internal constructions thereof.

FIGS. 11 through 13 are elevational views, partly in section, of an alternate embodiment of an introducer for the patch.

FIG. 14 is a perspective illustration of a patch delivery assembly constructed in accordance with a further alternate embodiment of the invention.

FIGS. 17 through 19 are elevational views, partly in section, of an introducer for the plug constructed in accordance with yet a further embodiment of the invention.

Similar reference numerals refer to similar parts throughout the various Figures.

DETAILED DESCRIPTION OF THE INVENTION

Overview

Figure 1:
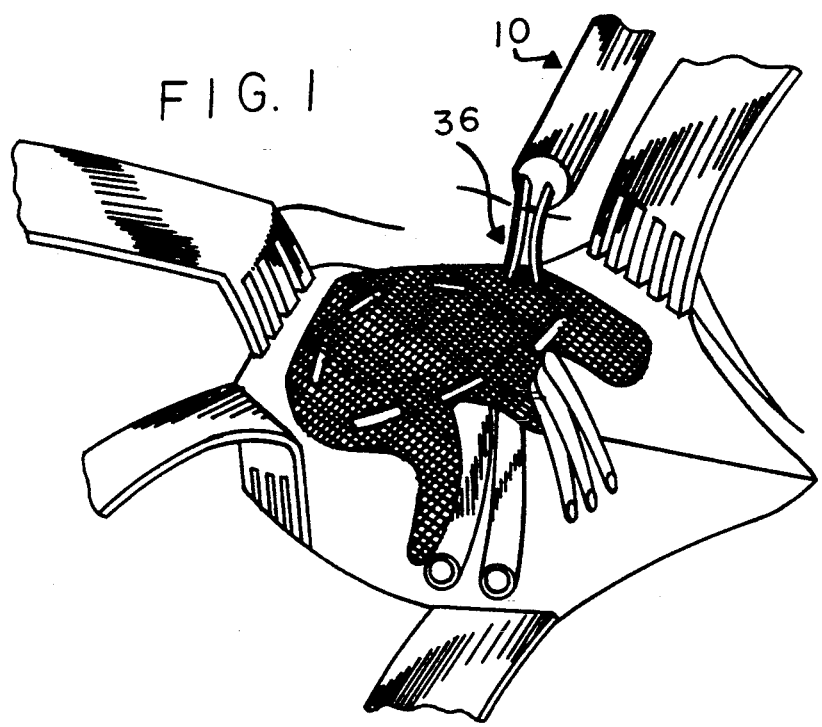
FIG. 1 shows a portion of the abdominal wall from the inside where hernias normally occur and also illustrating therein a patch for their repair and the precluding of further hernias.
Figure 3:
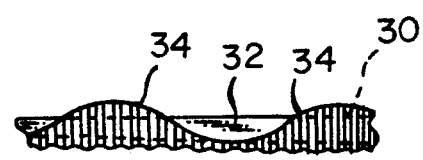
FIG. 3 is a sectional view of a portion of the patch shown in FIG. 2.

Shown in FIG. 1 is that portion of the abdomen where hernias normally occur. Whether through old age, accident, personal abuse, congenital problems, or the like, the inguinal floor of the abdomen known as Hesselbach's triangle may become weakened to the point whereby inner abdominal contents such as a bowel may protrude. When the organ extending therethrough is a portion of the bowel, serious illness or even death may occur. This is a direct inguinal hernia. There are two other common types of groin hernias. These occur adjacent to either the vas deferens (indirect) or the femoral vessels (femoral hernia). When either the internal inguinal ring through which the vas deferens passes or the abdominal wall adjacent to the femoral vessels becomes enlarged, an opening is created through which abdominal contents such as intestines may protrude thereby constituting a hernia. In the past, surgeons operated upon the hernia area either from above (preperitoneal) or below (anterior) with large incisions which lead to great disability.

The present invention includes introducers 10 with lugs 12 and patches 14, with the patches designed to cover all three areas where groin hernias normally occur and accomplishes a more physiological repair with a smaller incision utilizing laparoscopic technique by use of a specifically designed introducer and patch and preperitoneal approach presently not used.

Patch and Introducer

The patch 14 is preferably fabricated of a mono-filament thread which is woven, knitted or otherwise formed into a fabric which is then cut to a shape. It has a main central portion 16 to cover the inguinal floor area where direct groin hernias normally occur. The shape is generally in the shape of a trapezoid with a major axis and a minor axis.

Extending outwardly from one edge are three asymmetrical portions, formed as three fingers 18, 20 and 22 with the central finger being smaller than the other two. Formed between the fingers are spaced concave recesses, sized and positioned to be placed in close proximity to the vas deferens and or for the femoral vessels. Those portions of the patch located adjacent to the recesses are thus adapted to cover those areas of the abdomen where indirect and femoral hernias normally occur. At the same time, the central portion of the patch is adapted to cover the area of the inguinal floor where direct hernias normally occur.

The threads from which the patch is fabricated are of a surgically clean material which is durable, flexible, essentially inextensible and resistant to corrosion from bodily fluids. By way of example, one acceptable material is polypropaline such as Marlex ® mesh. Marlex is a trademark of the Johnson & Johnson Company of Somerville N.J. Further, by way of example, one acceptable material thread is Nylon ® polymer. Nylon is a registered trademark of E. I. DuPont deNemours Company of Wilmington, Del.

Formed into the patch is a passageway 30 for receiving a loop 32, the loop constituting the distal part of the patch delivery assembly or introducer 10. The passageway is shown in the preferred embodiment as spaced axial slits 34 through which the loop is threaded. The passageway may take other forms such as an elongated extent of fabric, preferably of the same material as the patch, secured in a symmetrical manner interior of the periphery of the patch.

When distended, the loop 32 is in the form of an ellipse which has a major axis and a minor axis coextensive with the major axis and minor axis of the patch. In the alternative, the loop and its passageway may taken one of many other forms such as that of a teardrop, circle or oval as shown in FIGS. 1, 2, 4, 5, 6, 12, 13 and 14. Other smoothly shaped, curved configurations could be utilized. The periphery of the patch is at varying distances from the passageway and loop. Hence the peripheral portions of the patch do not immediately reach all of the areas of direct as well as indirect hernias. Consequently, conventional laparoscopic techniques must be employed by the surgeon to provide final positioning of the patch after initial placement by the loop.

Figure 2:
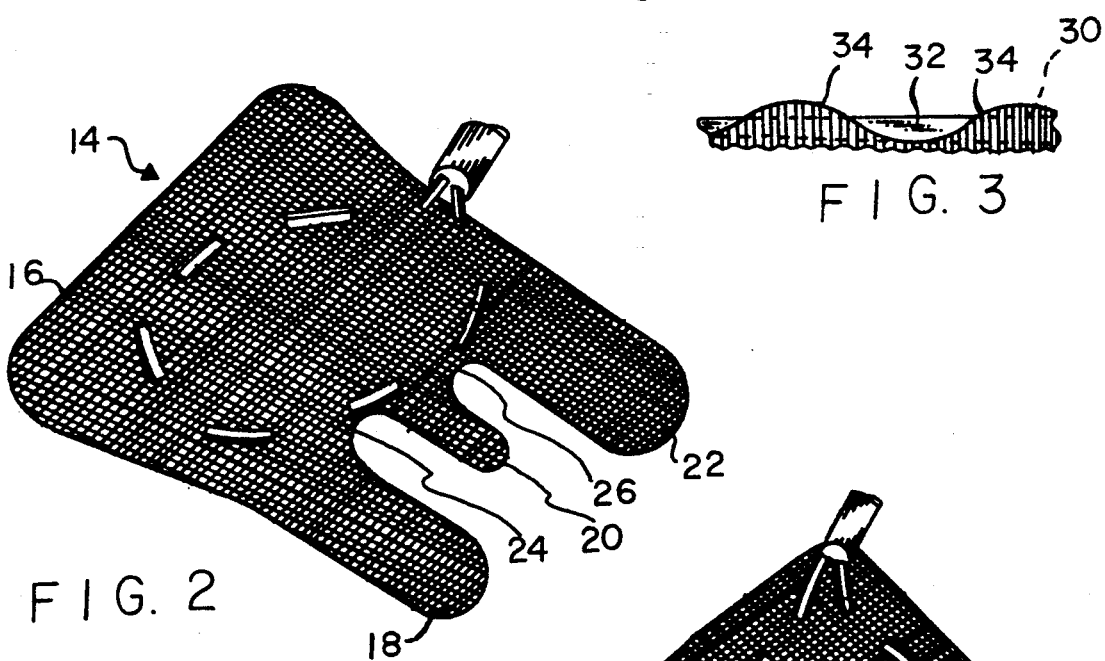
FIG. 2 is a perspective view of the patch constructed in accordance with the principles of the present invention and as shown in FIG. 1, shown in association with the patch is an introducer functioning as a delivery assembly for the patch.
Figure 4:
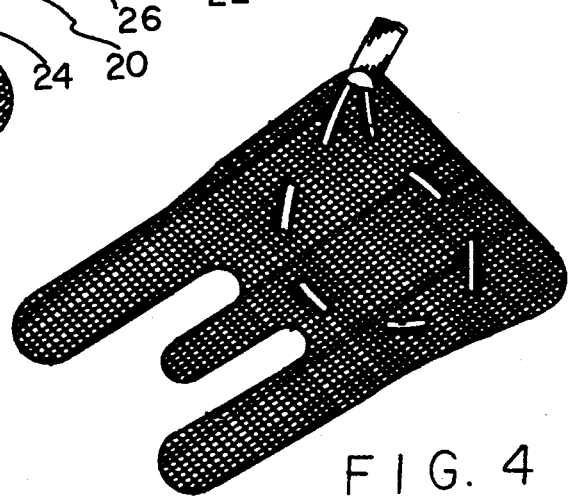
FIG. 4 is a perspective view of a patch similar to that of FIG. 2, but in mirror image for use on the other side of the patient and illustrating a smaller design as for a child.

Located within the passageway is the loop 32 of the ribbon 36, constructed of surgically antiseptic material and shaped in a smoothly curved configuration such as an ellipse when expanded. The loop 32 is of a size and configuration to be received within the passageway of the patch 14. The loop is at the far or distal end of the plunger 42. As shown in FIG. 2, the loop of the ribbon holds the majority of the patch is an extended orientation for initial placement of the abdominal wall over the hernia to be repaired. The proximal end of the loop is a ribbon extension of the loop which, like the loop, is flexible, but sufficiently rigid to function in association with the plunger 42 so that a surgeon may remotely push, pull, or rotate the loop and, consequently, the patch, during an operation. The plunger 42 includes a cylinder 44 and guide beam 46. The introducer 10 includes the plunger 42 and sheath 48.

The patch 14 as well as its supporting ribbon loop 32 and its distal extensions 52 are preferably prepackaged in a delivery assembly, the introducer 10, prior to use by insertion through a sleeve which is conventionally placed in a patient by a trochar.

Figure 7:
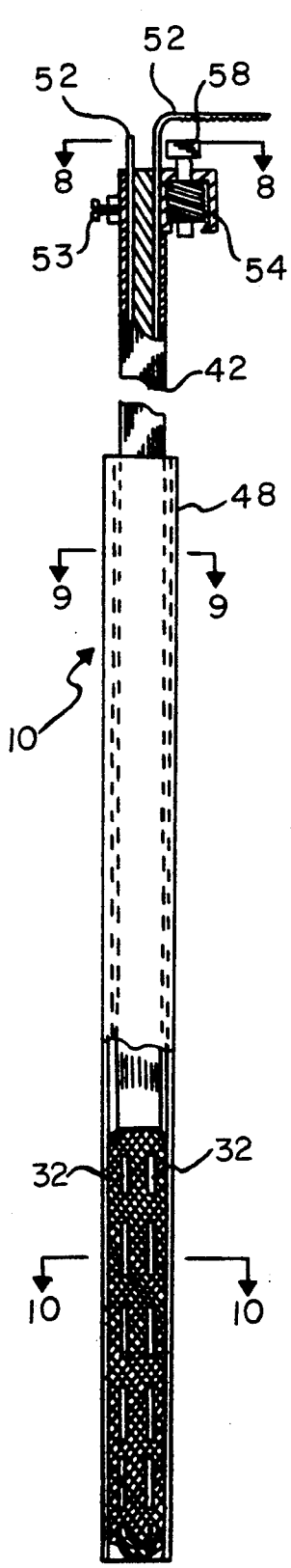
FIG. 7 is an elevational view, partly in section, of the introducer of FIGS. 2 through 6 but with the patch prior to discharge.
Figure 8:
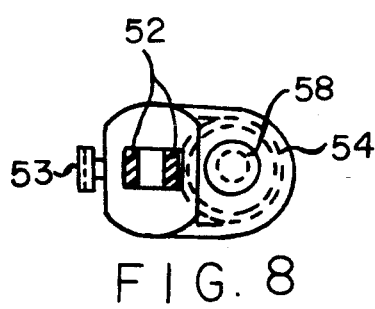
FIGS. 8 through 10 are sectional views of the introducer of FIG. 7 taken along lines 8—8, 9—9 and 10—10 of FIG. 7.
Figure 9:
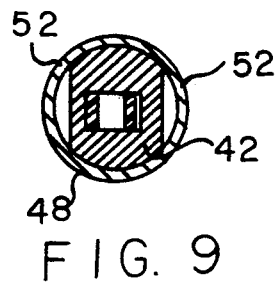
Figure 10:
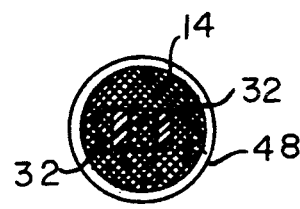

The delivery assembly 10 is best seen in FIG. 7. Its major components include an external cylindrical sheath 48 and an internal plunger 42. The proximal end of the plunger includes a set screw 52 oriented to releasably secure one end of the ribbon. The proximal end of the plunger/expander assembly 42 includes a worm gear 54 for coupling with teeth formed on the ribbon. Note FIG. 8. The worm gear 54 is a preferred mechanism since it permits precise adjustments in the moving of the loop and patch. In this manner, the surgeon may effect the precise movement of the loop in either direction but prevents the inadvertent movement thereof. A cylindrical guide beam 46 with flat faces is located interiorly along the length of the introducer 10 to act as a bearing surface during operation of the set screw 52 and worm gear 54 and for guiding the movement of the ribbon 36 with respect to the plunger 42 during the blooming of the patch. A weld 56, a dot of glue, or the like couples the proximal end of the patch to the distal end of the plunger.

In operation and use, the introducer 10 is inserted through the sleeve with its distal end adjacent to the area of the abdominal wall to be patched. The plunger-/expander 42 and patch 14 are pre-positioned within the sheath 48 as shown in FIG. 7. The introducer 10 then is moved forward by the surgeon moving the introducer with respect to the sleeve or withdrawing the sleeve with respect to the introducer. The ribbon, loop and patch move with the introducer when relative movement occurs between the sleeve and introducer. The plunger is depressed to dispense the main body of the patch. Thereafter, the surgeon rotates the knob 58 of the worm gear to enlarge the loop and cause the patch to bloom into the anatomically desired orientation as shown in FIGS. 1, 2 and 13. Using a second laproscopic opening, the surgeon will position the edges of the patch into final position. The patch will remain in position due to the pressure applied to it by the normal abdominal contents. Staples or sutures could be employed to further secure the patch in its final position.

Alternate Embodiment

The FIG. 11 through 13 embodiment illustrates an alternate introducer for holding the patch and for pushing it outwardly from the distal end of the sleeve. In this embodiment, the ribbon 62 is formed with an enlargement or block 64 at its distal end. The block has a slot 66 through which the ribbon passes to form a loop 68, in a manner similar to a lasso, which supports a patch 70 as in the prior embodiment. The slot is preferably formed with a ratchet tooth to sequentially engage ratchet teeth on the ribbon to allow for only one way movement of the ribbon during blooming of the patch.

The proximal end of the block is not coupled to the distal end of the plunger. Further, the proximal end of the patch is coupled to the distal end of the block as by a weld 74 to hold the proximal end of the patch in position as the distal end of the ribbon is moved distally to effect the blooming of the patch. The guide beam 76 has one flat side to receive and guide the ribbon 62 for movement with respect to the plunger cylinder 78 during the blooming of the patch 70.

In this embodiment, the distal end of the sheath 88 has axially slits 82 at a plurality of locations with the end forming a slight taper or bend. In this manner, the plunger 86 may be moved with respect to the sheath 88, from the FIG. 11 position to the FIG. 12 position. The surgeon can feel the slight resistance caused by the block 64 against the bend indicating that the FIG. 12 position has been reached. Thereafter, the proximal end of the ribbon may be fed distally with respect to the plunger and block to effect the blooming of the patch. Thereafter, the block is moved distally a greater distance until the FIG. 13 position is reached and the resistance to movement is no longer felt by the surgeon, thus freeing the patch from the introducer. The patch 70, loop 68 and block 64 are then cut free of the plunger 86 and the remainder of the ribbon.

Further Alternate Embodiment

In yet a further embodiment of the introducer 90, that shown in FIG. 14, the ribbon 92 is replaced by a looped mono-filament thread. The mono-filament thread is preferably of a surgically antiseptic, durable, inextensible material. By way of example, acceptable materials are Nylon, polypropyline and polyglycolic acid including PDS. PDS is a tradename of the Johnson and Johnson Company of Sommerville, N.J. These typical materials will allow the threads to be pushed from the introducer by the surgeon. The thread is shaped with a loop 94 received at its distal end. The proximal ends of the thread are for pushing and pulling the thread, and consequently blooming the patch, with respect to the plunger and sheath.

An intermediate portion of the thread is formed with an eyelet 96 adjacent to the proximal end of the plunger for the sliding passage of the proximal end of the thread. As in the embodiment discussed immediately hereinabove, the loop supporting the patch is formed as a lasso. The two proximal ends of the thread are manipulated by a surgeon during operation and use. A guide beam 98 shaped as an I-beam is incorporated within the plunger to guide the movement of the thread ends with respect to the plunger during the blooming of the patch. There is no need for a direct attachment of the loop to the plunger as this occurs passively. There is, however, a need for coupling the patch to the eyelet for proper patch placement. With the thread and patch dispensed outside the sheath as described above, the proximal end of the thread end passing through the eyelet is pushed so that a central extent of the thread begins to move forward out of the sheath to effect the blooming of the patch.

In all of the embodiments requiring thread removal, after final positioning of the patch, the proximal end of the patch must be cut from the its attachment from the introducer, block or eyelet ribbon while the distal end of the loop must be cut so that the introducer and ribbon may be withdrawn from the patch and site of the operation.

In the embodiments of FIGS. 4 and 11 through 13, when the loop is formed of an absorbable material, the loop must be cut free of the remainder of the ribbon.

It should be understood that a wide variety of mechanisms could be used to support the patch and to effect its blooming and positioning. In the disclosed embodiments herein, the mono-filament thread could be replaced by a ribbon and the ribbon could be replaced by a mono-filament thread. Further, a wide variety of materials could be substituted between the thread embodiment and ribbon embodiments including the use of absorbable, biodegradable or biocompatible materials for the loop that need not be removed. One typical material is polyglycolic acid.

Note is taken that the FIG. 14 embodiment illustrates the introducer 90 with a slight curve. This slight curve allows the surgeon to more readily axially rotate the introducer and thus the patch, for a more precise patch positioning. Such curve may also be utilized in the plug introducer assembly discussed hereinafter. Conventional straight or flexible sleeves may, of course, also be employed.

One distinguishing characteristic of the present invention is the shaping of the distal end of the introducer with a bevel 102. This will allow the surgeon to view the orientation if the introducer and patch on a monitor or through an operating laparoscope prior to moving the patch from the interior of the introducer. In addition, radiopaque markers 104 on the on the patch and/or plug could be utilized for determining their orientation and location by conventional radiographic techniques.

Plug and Introducer

Figure 15:
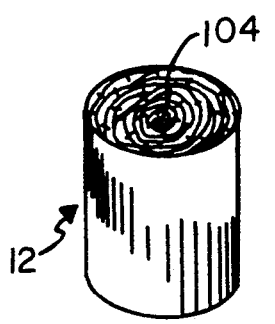
FIGS. 15 and 16 illustrate a plug usable independently of, or in association with, the apparatus shown in FIGS. 1 through 14.
Figure 16:
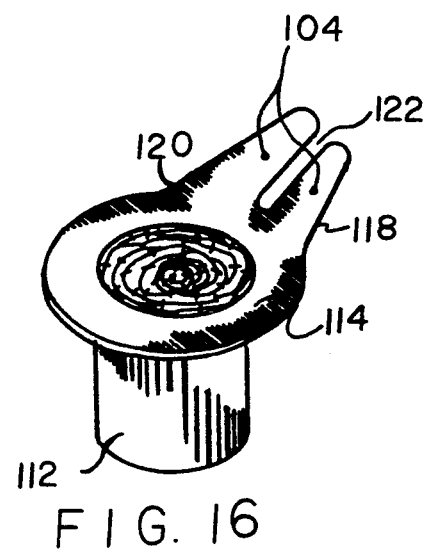

Plugs are shown in FIGS. 15 and 16 while their introducer 110 is shown in FIGS. 17 through 19. The FIG. 15 plug 12 is simply a patch of surgical fabric or mesh such as Marlex ® mesh. The material is spirally wrapped to form a mending component in a generally cylindrical shape. The term generally cylindrical shape is intended to include components which have a taper, as for example a truncated cone. It may also be fabricated as a one piece molded object.

The FIG. 16 plug 112 is similar in construction to the FIG. 15 plug 12. It includes, in addition, a flange 114. The flange is fabricated of a material similar to the patch. The flange may be with or without one peripheral edge that includes a radial extension with two symmetric fingers 118 and 120 and a recess 122 for receiving an adjacent vas deferens or femoral blood vessels. The central plug component may be of an absorbable or biodegradable material to be assimilated into bodily tissue over time. The plug is also preferably formed with openings or interstices to accelerate the healing of the opening being patched through the promoting of scar tissue in growth. The plug may be made of a material such that it expands and swells if exposed to fluids. A spongue is typical of such a material.

The plug introducer assembly 110 is seen in FIGS. 17, 18 and 19. Duration operation and use, the assembly is positioned through a sleeve. The assembly includes an exterior cylindrical sheath 128 and an interior cylindrical plunger 126. As seen in FIG. 17, the plug is initially located in the distal end of the sheath with the flange, if utilized, at the proximal end of the plug. The plunger is proximally located with respect to the plug.

As is conventional in the arts, laparoscopic sleeves or ports have an inner diameter of either 1.0 or 1.2 centimeters. Consequently, the plug diameter when packaged in the sheath, as shown in the various Figures, is slightly less than between 1.0 and 1.2 centimeters. The plug length is sufficient to be retained within the typical hernia defect which is generally of a length at least equal to the diameter of the plug, at least about 1.0 to 1.2 centimeters, the thickness of the abdominal musculature. Plugs may be greater in length depending on the requirement of the anatomy but should be as short as possible to avoid external palpation. In addition, the flange is about one to three times the radius of the plug, about 0.5 to 1.5 centimeters, measured radially from the radially exterior of the plug. The flanges may be greater in size, twice as large as shown or even larger, depending upon the nature of the anatomy and the body portions available to which the flange will be secured to the patient.

In operation and use, the distal end of the introducer and plug is simply inserted into the hernia defect 132 and dispensed by depressing the plunger. This withdraws the sheath leaving the plug in place. Additional plugs may be placed to fill the defect if excessively large. Alternatively the plug with flange may be inserted to plug the defect and support the adjacent weak tissue. The dispensing of the plug may be effected by any relative movement between the plunger and sheath by moving the plunger with respect to the sheath or the sheath with respect to the plunger. FIG. 1B illustrates the plug in the tissue opening after being dispensed. FIG. 19 illustrates the plug with a flange. Handles at the proximal ends of the sheath and plunger assist the surgeon in this procedure. Once place within the tissue to be repaired, the plug or plugs may be caused to swell to a larger diameter through being irrigated either naturally through bodily fluids or artificially as through a saline solution introduced by the surgeon.

Method

The plug and patch and their delivery apparatus may be utilized independently of each other or sequentially in system configuration, depending on the condition of the patient and the parts of the body to be repaired. The utilized mending component, whether plug or patch, are at the discretion of the surgeon.

During an operation, the operating laparoscope, sleeve with its contents, is positioned within the incision into the preperitoneal space. The space is dissected with insulflation of carbon dioxide or other conventional gas technique. The laparoscope and its contents are manipulated inwardly and outwardly thereof for effecting the appropriate procedures. After dissection of the space other punctures in the abdomen are made for placement of a second or third sleeve. These additional sleeves allow use of additional instruments for manipulation, dissection, and use of a laser or cautery. Similarly, the patch and/or plug introducers and contents are manipulated inwardly and outwardly of the sleeves.

To position the plug in its adjacent to the intended area, the plug is positioned within the distal end of the introducer. The plug is initially packaged within the introducer. The introducer and its contents are advanced to within the hernia defect which is to receive the plug. The surgeon pushes the proximal end of the plunger forward while the sheath is held against movement. The plug will then move outside of the sheath into the position of FIG. 18. The sheath is then withdrawn while holding the plug against movement while allowing complete release from the sheath. Additional plugs may be inserted as needed.

To position the patch in its orientation adjacent to the intended area, the patch is positioned on the loop and located within the distal end of the introducer. The patch and loop are initially packaged within the introducer. The introducer and its contents are advanced to a position adjacent to the area of the abdominal wall which is to receive the patch. The patch is dispensed by the surgeon pushing the proximal end of the plunger forward while the sheath is held against movement. The patch will then move outside of the introducer with the loop resiling to the elliptical shape of FIGS. 1 and 2. The blooming of the patch is effected by the extending of the loop within the patch thus distending the patch to proper, anatomically correct shape. This procedure may be observed by the surgeon through conventional laparoscopic techniques.

With the central portion of the patch properly positioned, the surgeon may manipulate the edges of the patch exterior of the loop, and secure the patch in proper position. Staples or sutures could be utilized but the contents of the abdominal cavity may be sufficient to apply adequate pressure to hold the patches in proper position.

With the patch having been secured around its periphery as shown in FIG. 1, the ribbon may be removed from the patch prior to the withdrawal of the introducer. Once again, conventional laparoscopic techniques may be employed to cut the ribbon at its distal end so that the ribbon may be slide from the passageway and withdrawn prior to removal of the introducer. This step is eliminated if the loop is of a degradable material. The patch and loop must then be cut away from the plunger prior to removal of the introducer.

The present invention may be utilized by a surgeon in carrying out a new laparoscopic procedure for repairing hernias.

The present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

What is claimed is:

1. Apparatus for the repair of hernias through laparoscopic techniques comprising a tubular sheath and a tubular plunger located within and moveable with respect to the sheath, the plunger having a distal end, and a generally cylindrical plug with a flexible patch at a proximal end of the plug supported within the sheath, a distal end of the plug being located adjacent to a distal end of the sheath with the patch proximally thereof, the plug adapted to be discharged from the sheath upon relative axial movement between the plunger and sheath, the plunger having an end extending proximally of the sheath for manipulation by a surgeon.

2. Apparatus for the plugging of the hernias through laparoscopic techniques comprising:
    a tubular sheath having a distal end and a proximal end;
    a tubular plunger located within and moveable with respect to the sheath, the plunger having a distal end spaced proximally of the distal end of the sheath and a proximal end extending proximally of the proximal end of the sheath; and
    a non-tubular plug having an essentially cylndrical configuration along its entire length, the plug being located within the sheath at the distal end and moveable from interior thereof to exterior thereof upon manipulation of the proximal ends of the plunger and sheath by a surgeon, the plug being fabricated of a material adapted to be assimilated into bodily tissue over time and adapted to expand and swell when exposed to fluids.

3. Apparatus for laparoscopically patching hernias comprising:
    a tubular sheath having a distal end and a proximal end;
    a tubular plunger located within and moveable with respect to the sheath, the plunger having a proximal end and a distal end with the proximal end of the plunger extending proximally outwardly of the sheath for manipulation by a surgeon;
    elongated means, having a distal end and a proximal end, forming part of the plunger at the distal end of the plunger and forming a loop, the proximal end of the elongated means extending proximally outwardly of the sheath for manipulation by a surgeon; and
    a patch supported on the loop for movement therewith, the patch having a passageway for receipt of the loop to retain the patch in a planar configuration.

4. The apparatus as set forth in claim 3 wherein the elongated means comprises a ribbon shaped member.

5. The apparatus as set forth in claim 4 and further including a worm gear for moving the elongated means with respect to the plunger.

6. The apparatus as set forth in claim 4 and further including an enlargement at one end of the elongated means with a slot through which the ribbon shaped member passes to form the loop.

7. The apparatus as set forth in claim 3 wherein the elongated means is a thread.

8. The apparatus as set forth in claim 7 and further including an eyelet formed in an intermediate portion of the thread through which the thread passes to form the loop.

9. The apparatus as set forth in claim 3 wherein the loop is formed of an absorbable material.

10. The apparatus as set forth in claim 3 and further including means securing the proximal end of the patch to the plunger.

11. The apparatus as set forth in claim 3 and further including a component within the lunger for guiding the movement of the ribbon with respect to the plunger during the blooming of the patch.

12. The apparatus as set forth in claim 3 wherein the loop is formed of flexible material.

13. A patch for positioning over the regions of a floor of an abdominal cavity normally susceptible to hernias, the patch having a proper anatomical shape with a plurality of radially extending portions forming spaced recesses for the receipt of a vas deferens, testicular artery and vein and femoral vessels, the patch also having a passageway in a curved, symmetrical configuration adjacent to its periphery for the receipt of a smoothly curved loop for maintaining the patch and loop in a planar orientation.

14. A plug for positioning in hernial openings of an abdominal cavity and similar openings, the plug being of a generally cylindrical shape with a distal end and a proximal end and a generally elliptical flange on the proximal end of the plug and two fingers extending radially from the flange with a recess therebetween.

15. A system for the repair of hernias through laparoscopic techniques including plugging and patching, the system comprising:
    a first assembly having a tubular sheath with a distal end and a proximal end; a tubular plunger with a distal end and a proximal end, the plunger being located within and moveable with respect to the sheath, the plunger having a distal end spaced proximally of the distal end of the sheath and a proximal end extending proximally of the proximal end of the sheath; a plug within the sheath at the distal end and moveable from interior thereof to exterior thereof upon manipulation of the proximal ends of the sheath and plunger by a surgeon; and
    a second assembly having another tubular sheath; another tubular plunger located within and moveable with respect to the other sheath, the proximal end of the other plunger extending proximally outwardly of the other sheath for manipulation by a surgeon; elongated means extending through the other plunger and, at the distal end thereof forming an expandable loop, the proximal end of the elongated means extending proximally outwardly of the other sheath for manipulation by a surgeon; and a patch supported on the loop for movement and expansion therewith.

16. A method for the plugging of a hernia opening through laparoscopic techniques comprising the steps of:

providing a tubular sheath having a distal end and a proximal end with an outer diameter to slide within a laparoscopic port;

providing a tubular plunger located within and moveable with respect to the sheath, the plunger having a distal end spaced proximally of the distal end of the sheath and a proximal end extending proximally of the proximal end of the sheath;

providing a cylindrical, non-tubular plug having an outer diameter to fit within the tubular sheath and having a flange at a proximal end of the plug with a radial dimension of at least the radius of the plug, the plug being located within the sheath with a distal end of the plug at the distal end of the sheath and its proximal end proximally thereof;

inserting the distal end of the plunger along with the sheath through a laparoscopic port into a patient's abdominal wall musculature, positioning the distal end of the sheath and plug adjacent to the hernia opening to be repaired;

effecting relative motion between the sheath and plunger to discharge the plug into the opening to be repaired;

coupling the flange to the abdominal wall; and removing the plunger and sheath from the abdominal wall musculature through the laproscopic port.

17. A method for the plugging of a hernia opening through laparoscopic techniques comprising the steps of:

providing a tubular sheath having a distal end and a proximal end with an outer diameter to slide within a laparoscopic port;

providing a tubular plunger located within and moveable with respect to the sheath, the plunger having a distal end spaced proximally of the distal end of the sheath and a proximal end extending proximally of the proximal end of the sheath, providing a non-tubular plug with a generally cylindrical configuration and having an outer diameter to fit within the tubular sheath, the plug being located within the sheath with a distal end of the plug adjacent to the distal end of the sheath, inserting the distal ends of the plunger, sheath and plug through a laparoscopic port and through a patient's abdominal wall to interior of the patient's abdominal musculature;

positioning the distal end of the sheath and plug adjacent to the hernia opening to be repaired;

effecting relative motion between the sheath and plunger to discharge the plug into the opening to essentially fill the hernia opening, and removing the plunger and sheath from the abdominal cavity through the laproscopic port.

* * * * *